April 23, 1968 B. A. HOEKMAN Plant Pat. 2,806

APPLE TREE

Filed Nov. 21, 1966 3 Sheets-Sheet 1

INVENTOR.
BUD A. HOEKMAN
BY
Christensen, Sanborn & Matthews
ATTORNEYS

APPLE TREE

Filed Nov. 21, 1966 3 Sheets-Sheet 2

INVENTOR
BUD A. HOEKMAN
BY
Christensen, Sanborn & Matthews
ATTORNEYS

INVENTOR.
BUD A. HOEKMAN
BY
Christensen, Sanborn & Matthews
ATTORNEYS

United States Patent Office

Plant Pat. 2,806
Patented Apr. 23, 1968

2,806
APPLE TREE
Bud A. Hoekman, Zillah, Wash. 98953
Filed Nov. 21, 1966, Ser. No. 596,023
1 Claim. (Cl. Pit.—34)

ABSTRACT OF THE DISCLOSURE

Discovered as a chance seedling in a cultivated orchard, this new variety produces fruit resembling Golden Delicious, but differing therefrom in flavor, firmness, color and surface finish. Less upright in growth than Starking Delicious, the tree is not as spreading as Golden Delicious. Other distinguishing features are also noted.

*Background of discovery*

The present new variety of apple tree was discovered as a chance seedling originating and growing in applicant's orchard at Zillah, Yakima County, State of Washington. This orchard consisted of Starking Delicious and Golden Delicious trees planted in the year 1955. In connection with the discovery of this seedling, it was noticed that it bore fruit which was generally similar to Golden Delicious, but different in fruit flavor, surface finish, color and firmness. It was also noted that the fruit of this seedling tree colored earlier, more uniformly and developed a greater color intensity than the fruit of adjacent Golden Delicious trees. Further, it was observed that this seedling differed from Golden Delicious in habit of growth, color of bark and color and shape of leaves.

Closer inspection revealed that this newly discovered chance seedling tree is indeed a new and distinctive variety. Succeeding generations of the tree produced by asexual reproduction thereof (from buds) have demonstrated the genetic stability of its characterizing features.

This new variety of apple tree is characterized as to novelty by unique combinations of features which distinguish it from the nearest known or related varieties as hereinafter more specifically described and illustrated with reference to the accompanying drawings.

*Detailed description*

Figure 1:
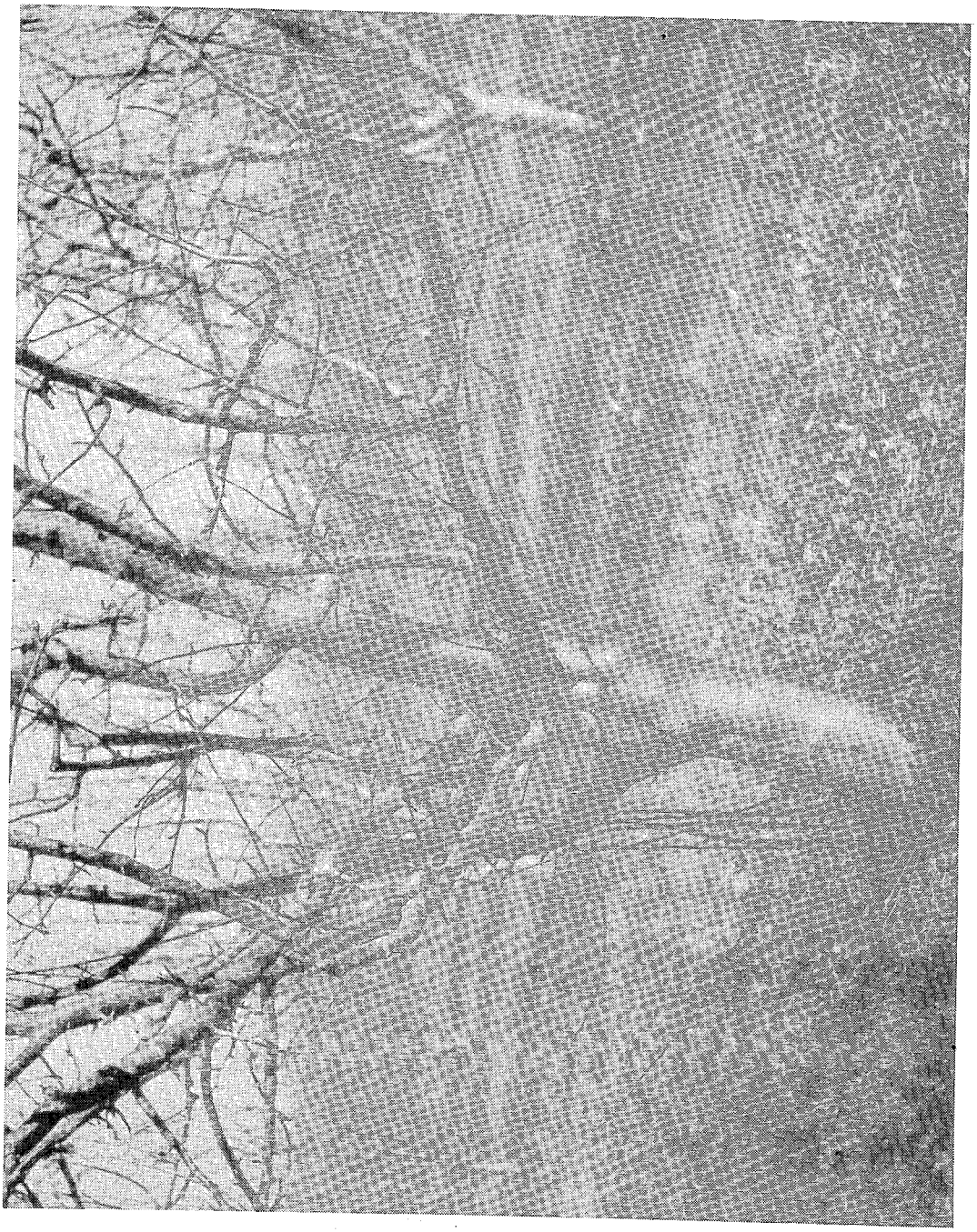
FIGURE 1 is a black-and-white photographic print of the original seedling tree as discovered in the above-mentioned orchard.
Figure 2:
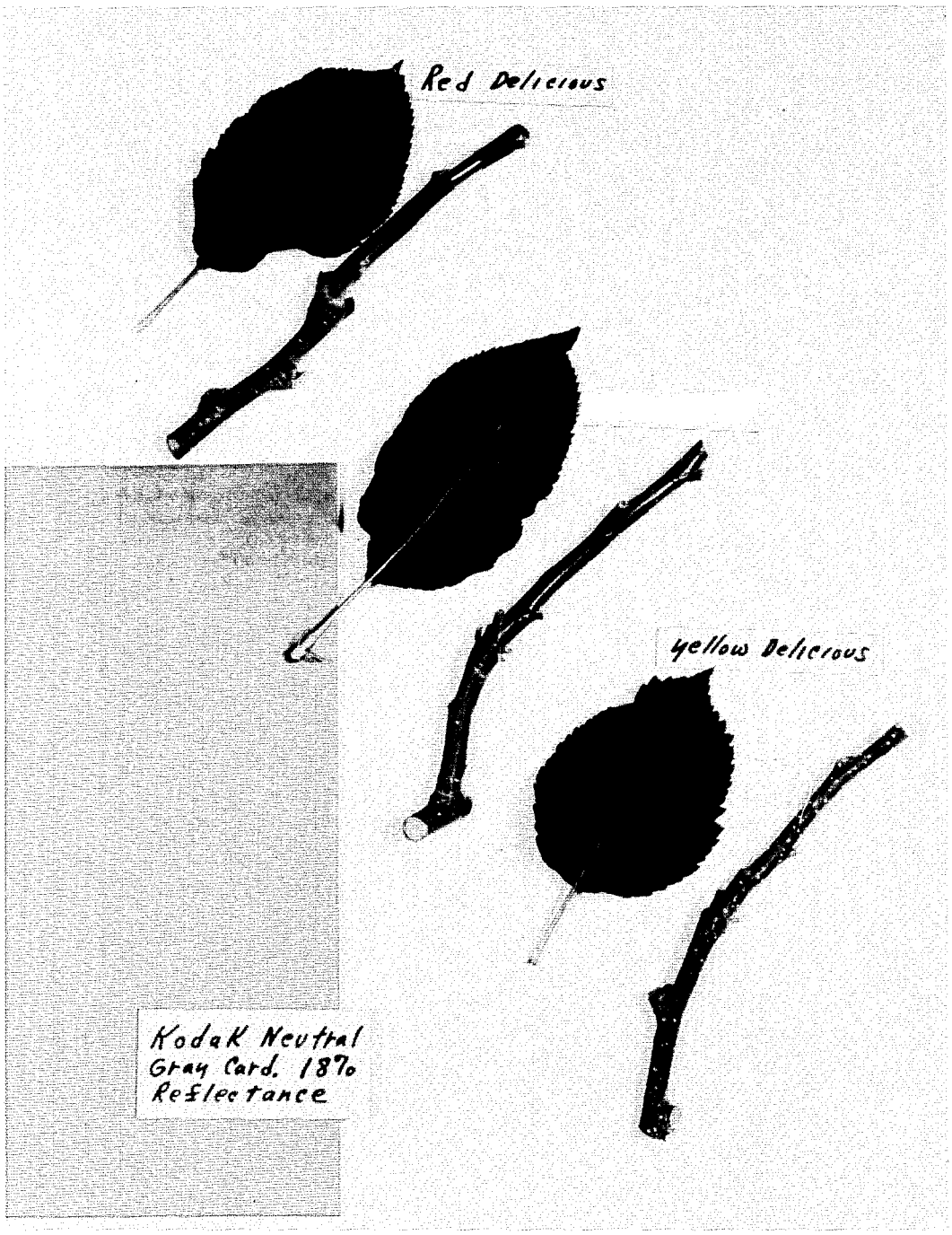
FIGURE 2 is a color photographic print in which the leaf and a twig section of the new variety are displayed side-by-side with those of the Standard Red or Starking Delicious and the Golden or Yellow Delicious as labeled.
Figure 3:
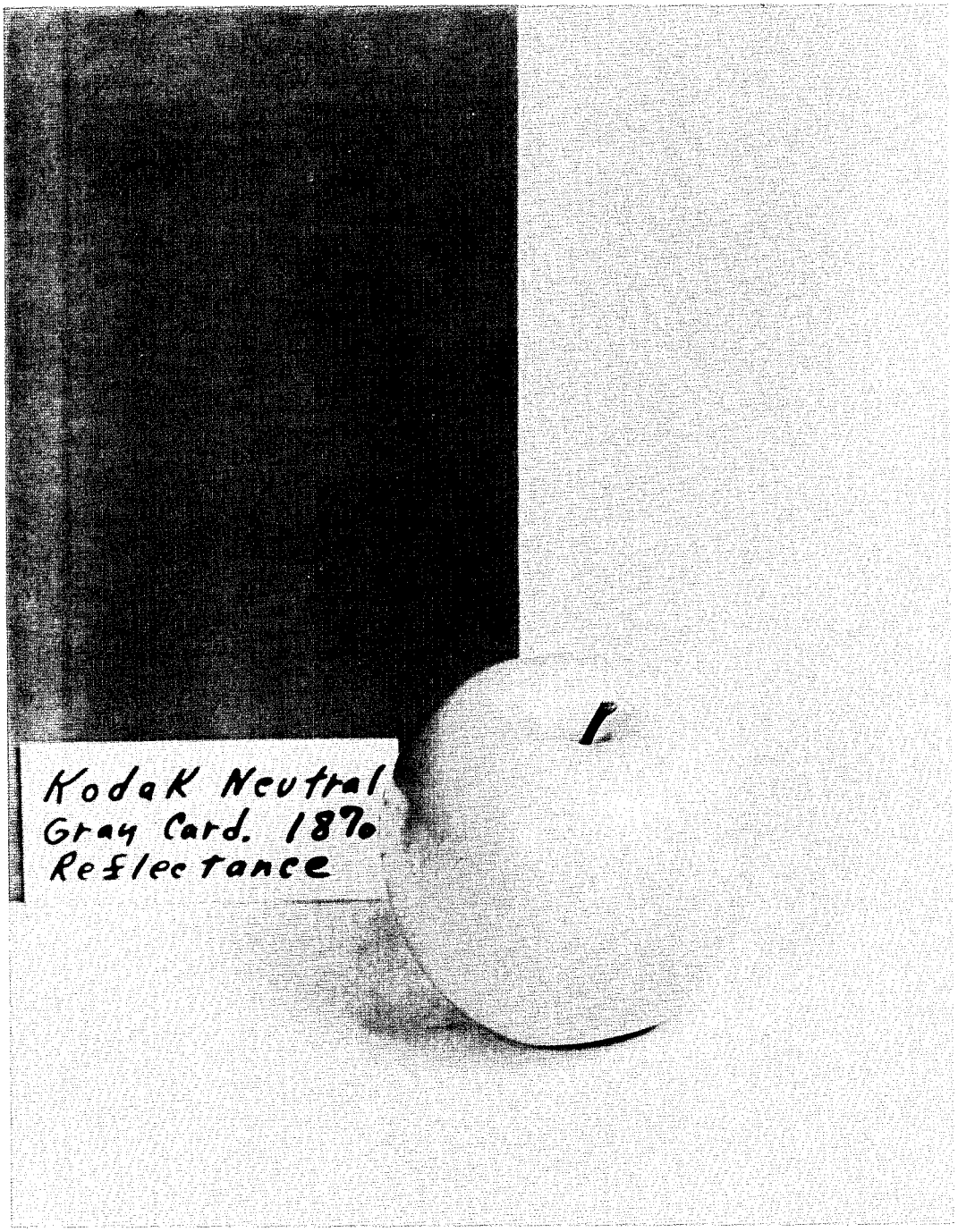
FIGURE 3 is a color photographic print of a representative apple of the new variety at a stage of substantially full coloration and ripeness for picking.

Tree: Medium vigor. Less upright than Starking Delicious, but not as spreading as Golden Delicious.

*Trunk.*—Smooth; stocky.

*Branches.*—Limbs form moderately wide angles with central axis. Lenticels less numerous than on Golden Delicious but somewhat more numerous than on Starking Delicious branches. Bark is similar in color to Starking Delicious.

*Leaves.*—Approximately same size and shape as those of Golden Delicious, but somewhat darker green when grown under the same cultural conditions. Serrations of leaves along margin are extremely fine and sharp as compared with those of Golden Delicious.

Flowers:

*Size.*—Medium size.

*Color.*—White with portions of petals tinged with pink—similar to Starking Delicious.

*Time of full bloom.*—Three to five days after Golden Delicious.

Fruit:

*Maturity.*—Fruit matures at about the same time as Golden Delicious. When picked at the same stage of color as Golden Delicious and held at cold (32° F.) and warm (70° F.) temperatures, the fruit of this new variety takes on an intense yellow color much sooner than Golden Delicious.

*Firmness and keeping quality.*—Very firm; resistant to bruising. Maintains firmness in storage longer than Golden Delicious as measured by pressure tester. Does not shrivel in storage.

*Size.*—Variable. Axial diameter 3 to 4 inches. Transverse diameter 2¾ inches to 3¾ inches.

*Form.*—Truncate at base; slightly conical.

*Cavity.*—Acute to obtuse; wide, medium depth.

*Basin.*—Symmetrical; wide, median depth; slight corrugated.

*Stem.*—Long; slender; pubescent.

*Calyx.*—Partly closed; segments persistent; reflexed from base to apex.

*Skin.*—Very smooth, russett free; waxy. Dots small, depressed, inconspicuous. Color—yellow color substantially Color I-1, Plate 17, page 57, Dictionary of Color by Marez and Paul, 1st ed. 1930. Bloom wanting.

*General color effect.*—Intense yellow.

*Flesh.*—Juicy; white; firm. Flavor mild; slightly subacid. Aroma distinct. Quality—best.

*Core.*—Median. Bundle area large; symmetrical; broad at base. Halves of core—equal. Bundles inconspicuous, tinged with green. Core lines clasping. Capillary area—distinct; medium. Calyx tube short (¼″), cone-shaped. Styles present—not united at base. Stamens—median. Seed cells—medium, open.

Seed: Number, 5–8; all perfect.

*Form.*—Acute.

*Color.*—Dark brown.

Potential use: Dessert; culinary.

Keeping quality: Good—3 to 7 months at 31° F.

I claim:

1. A new and distinct variety of apple tree, substantially as herein shown and described.

No references cited.

ROBERT E. BAGWILL, *Primary Examiner.*